US011276168B2

(12) United States Patent
Sabina et al.

(10) Patent No.: US 11,276,168 B2
(45) Date of Patent: *Mar. 15, 2022

(54) REGISTRATION OF NON-OVERLAPPING INTRAORAL SCANS

(71) Applicant: Align Technology, Inc., San Jose, CA (US)

(72) Inventors: Michael Sabina, Campbell, CA (US); Leon Rasovsky, Mountain View, CA (US)

(73) Assignee: Align Technology, Inc., San Jose, CA (US)

( * ) Notice: Subject to any disclaimer, the term of this patent is extended or adjusted under 35 U.S.C. 154(b) by 79 days.

This patent is subject to a terminal disclaimer.

(21) Appl. No.: 16/808,239

(22) Filed: Mar. 3, 2020

(65) Prior Publication Data
US 2020/0202528 A1    Jun. 25, 2020

Related U.S. Application Data

(63) Continuation of application No. 16/155,754, filed on Oct. 9, 2019, now Pat. No. 10,621,723, which is a (Continued)

(51) Int. Cl.
*G06T 7/00* (2017.01)
*G06T 7/30* (2017.01)
(Continued)

(52) U.S. Cl.
CPC .............. *G06T 7/0012* (2013.01); *A61B 6/14* (2013.01); *A61C 7/002* (2013.01); *A61C 9/0046* (2013.01);
(Continued)

(58) Field of Classification Search
CPC .......... A61B 6/14; G06T 7/0012; G06T 7/11; G06T 7/30; G06T 17/00;
(Continued)

(56) References Cited

U.S. PATENT DOCUMENTS

| 5,775,912 A | 7/1998 | Panzera et al. |
| 7,590,462 B2 | 9/2009 | Rubbert et al. |

(Continued)

FOREIGN PATENT DOCUMENTS

| CA | 2315716 C | 12/2008 |
| CN | 105447908 A | 3/2016 |

OTHER PUBLICATIONS

International Search Report and Written Opinion of International Application No. PCT/US2017/035820 dated Aug. 17, 2017, 14 pages.

*Primary Examiner* — Katrina R Fujita
(74) *Attorney, Agent, or Firm* — Lowenstein Sandler LLP

(57) ABSTRACT

A processing device receives first intraoral scan data of a first segment of a dental site and second intraoral scan data of a second segment of the dental site that does not stitch to the first intraoral scan data of the first segment of the dental site. The processing device generates a first virtual model of the first segment using the first intraoral scan data, and further generates a second virtual model of the second segment using the second intraoral scan data. The processing device arranges a spatial relationship of the first virtual model and the second virtual model.

20 Claims, 6 Drawing Sheets

Related U.S. Application Data continuation of application No. 15/199,437, filed on Jun. 30, 2016, now Pat. No. 10,136,972.

(51) Int. Cl.
| | | |
|---|---|---|
| *G06T 7/11* | (2017.01) | |
| *A61C 9/00* | (2006.01) | |
| *A61C 13/00* | (2006.01) | |
| *A61B 6/14* | (2006.01) | |
| *A61C 7/00* | (2006.01) | |
| *G06K 9/62* | (2006.01) | |
| *G06T 17/00* | (2006.01) | |

(52) U.S. Cl.
CPC ........ *A61C 9/0053* (2013.01); *A61C 13/0004* (2013.01); *G06K 9/6202* (2013.01); *G06T 7/11* (2017.01); *G06T 7/30* (2017.01); *G06T 17/00* (2013.01); *G06T 2207/30036* (2013.01)

(58) Field of Classification Search
CPC .......... G06T 2207/30036; A61C 7/002; A61C 9/0046; A61C 9/0053; A61C 13/0004; G06K 9/6202
See application file for complete search history.

(56) References Cited

U.S. PATENT DOCUMENTS

| | | | |
|---|---|---|---|
| 7,695,278 | B2 | 4/2010 | Sporbert et al. |
| 7,916,911 | B2 | 3/2011 | Kaza et al. |
| 10,653,503 | B2 * | 5/2020 | Boltunov ............... A61C 9/004 |
| 10,835,361 | B2 * | 11/2020 | Fisker ................... A61B 5/1111 |
| 2006/0072810 | A1 | 4/2006 | Scharlack et al. |
| 2007/0171220 | A1 * | 7/2007 | Kriveshko ........... A61C 9/0046 |
| | | | 345/419 |
| 2007/0172112 | A1 | 7/2007 | Paley et al. |
| 2010/0303341 | A1 | 12/2010 | Hausler |
| 2011/0070554 | A1 | 3/2011 | Kopelman et al. |
| 2011/0125304 | A1 | 5/2011 | Schneider et al. |
| 2012/0015316 | A1 | 1/2012 | Sachdeva et al. |
| 2013/0110469 | A1 | 5/2013 | Kopelman |
| 2014/0120493 | A1 | 5/2014 | Levin |
| 2014/0335470 | A1 | 11/2014 | Fisker et al. |
| 2015/0007830 | A1 * | 1/2015 | Remmers ............. A61B 5/4818 |
| | | | 128/848 |
| 2015/0209118 | A1 | 7/2015 | Kopelman et al. |
| 2015/0320320 | A1 | 11/2015 | Kopelman et al. |
| 2015/0359615 | A1 | 12/2015 | Sabina et al. |
| 2016/0008116 | A1 * | 1/2016 | Glinec ................... G06T 19/20 |
| | | | 433/29 |
| 2016/0135925 | A1 * | 5/2016 | Mason ................... A61C 7/002 |
| | | | 703/2 |
| 2016/0163115 | A1 | 6/2016 | Furst |

\* cited by examiner

REGISTRATION OF NON-OVERLAPPING INTRAORAL SCANS

RELATED APPLICATIONS

The present application is a continuation of U.S. patent application Ser. No. 16/155,754, filed Oct. 9, 2018, which is a continuation of U.S. patent application Ser. No. 15/199,437, filed Jun. 30, 2016, both of which are incorporated by reference herein.

TECHNICAL FIELD

Embodiments of the present invention relate to the field of intraoral scanning and, in particular, to a system and method for improving the efficiency and accuracy of intraoral scanning.

BACKGROUND in both prosthodontic and orthodontic procedures, obtaining a three-dimensional (3D) model of a dental site in the oral cavity is an initial procedure that is performed. In orthodontic procedures it can be important to provide a model of one or both jaws. 3D models created by the use of a 3D modeling scanner (e.g., a scanning wand) aid in the accurate creation of molds for corrective work. Scans may typically be performed when a patient comes in for a progress update check, to receive additional treatment, or sometimes during a routine hygiene appointment. Historically, each scan for a particular patient is treated as a new scan, unrelated to past scans of the same patient.

Additionally, scans have historically been cumbersome and time consuming. 3D scans rely on being able to stitch (hereafter referred to as "register") images of a scan session captured by a scanner to generate an accurate and complete 3D model. Frequently, images of a scan session may not be registered due to insufficient overlap between images. Images that cannot be registered to another image of the scan session are discarded, and a user interrupts the session to rescan any discarded areas. Furthermore, many scanners have a difficult time initializing after an interruption due to insufficient overlap between images or excessive wand movement. Such limitations are frustrating and impose additional time to work through.

BRIEF DESCRIPTION OF THE DRAWINGS

The present invention is illustrated by way of example, and not by way of limitation, in the figures of the accompanying drawings.

DETAILED DESCRIPTION

Figure 1:
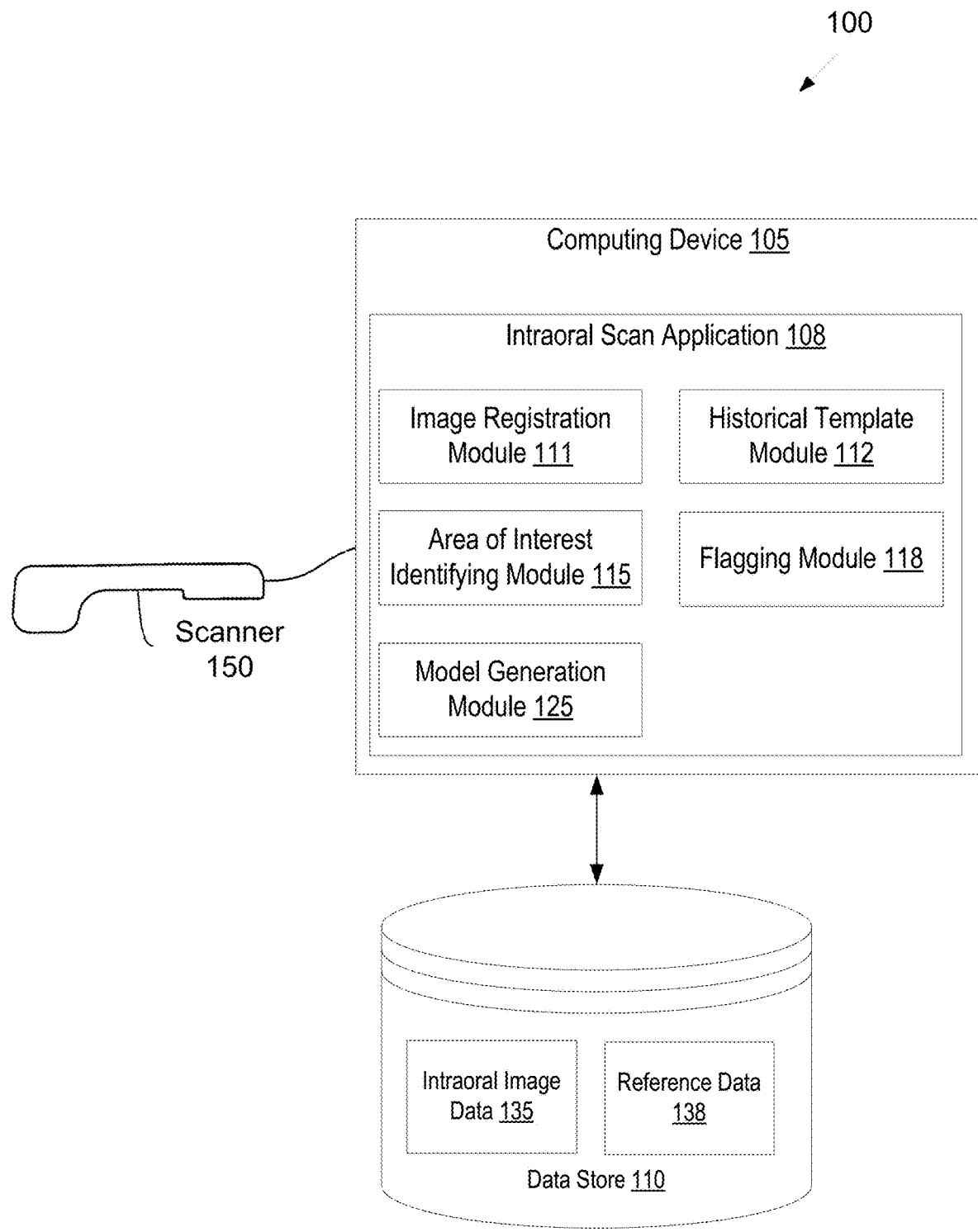
FIG. 1 illustrates one embodiment of a system for performing intraoral scanning and generating a virtual three dimensional model of a dental site.

Described herein is a method and apparatus for improving the quality of scans, such as intraoral scans taken of dental sites for patients. During a scan session, a user (e.g., a dental practitioner) of a scanner may generate multiple different images (also referred to as scans) of a dental site, model of a dental site, or other object. The images may be discrete images (e.g., point-and-shoot images) or frames from a video (e.g., a continuous scan). These images may not capture all of the areas of the dental site and/or there may be areas for which there is conflicting data between images. For example, images recorded during a scan session may not be adequately registered to other images, thus yielding an incomplete arrangement of images of the scan session. Historically, images that cannot or should not be registered to other images in the scan session may be discarded, leaving the user to rescan the areas not captured. In embodiments described herein, such images are registered to a template that is based on a prior scan. This can facilitate quick and accurate scan sessions by reducing or eliminating discarded images. Additionally, during a scan session regions of a dental site that have been scanned in the scan session may be registered to the historical template and displayed in relation to the historical template in a three dimensional image. Current scan data may be represented using first imagery (e.g., solid surfaces) and historical scan data may be represented using second imagery (e.g., translucent surfaces or pixelated surfaces). As additional intraoral images are received during the scan session, these intraoral images may be registered to previously received intraoral images from the current scan session or to the historical template. The three dimensional image may then be updated to reflect the new intraoral images.

Embodiments described herein are discussed with reference to intraoral scanners, intraoral images, intraoral scan sessions, and so forth. However, it should be understood that embodiments also apply to other types of scanners than intraoral scanners. Embodiments may apply to any type of scanner that takes multiple images and registers these images together to form a combined image or virtual model. For example, embodiments may apply to desktop model scanners, computed tomography (CT scanners, and so forth. Additionally, it should be understood that the intraoral scanners or other scanners may be used to scan objects other than dental sites in an oral cavity. For example, embodiments may apply to scans performed on physical models of a dental site or any other object. Accordingly, embodiments describing intraoral images should be understood as being generally applicable to any types of images generated by a scanner, embodiments describing intraoral scan sessions should be understood as being applicable to scan sessions for any type of object, and embodiments describing intraoral scanners should be understood as being generally applicable to many types of scanners.

FIG. 1 illustrates one embodiment of a system 100 for performing intraoral scanning and/or generating a virtual three dimensional model of a dental site. In one embodiment, system 100 carries out one or more operations below described in method 200. System 100 includes a computing device 105 that may be coupled to a scanner 150 and/or a data store 110.

Computing device 105 may include a processing device, memory, secondary storage, one or more input devices (e.g., such as a keyboard, mouse, tablet, and so on), one or more output devices (e.g., a display, a printer, etc.), and/or other hardware components. Computing device 105 may be connected to a data store 110 either directly or via a network. The network may be a local area network (LAN), a public wide area network (WAN) (e.g., the Internet), a private WAN (e.g., an intranet), or a combination thereof. The computing device 105 may be integrated into the scanner 150 in some embodiments to improve performance and mobility.

Data store 110 may be an internal data store, or an external data store that is connected to computing device 105 directly or via a network. Examples of network data stores include a storage area network (SAN), a network attached storage (NAS), and a storage service provided by a cloud computing service provider. Data store 110 may include a file system, a database, or other data storage arrangement.

In some embodiments, a scanner 150 for obtaining three-dimensional (3D) data of a dental site in a patient's oral cavity is operatively connected to the computing device 105. Scanner 150 may include a probe (e.g., a hand held probe) for optically capturing three dimensional structures (e.g., by confocal focusing of an array of light beams). One example of such a scanner 150 is the iTero® intraoral digital scanner manufactured by Align Technology, Inc. Other examples of intraoral scanners include the 1M™ True Definition scanner, the Apollo DI intraoral scanner, the CEREC AC intraoral scanner manufactured by Dentsply Sirona®, and the Trios® intraoral scanner manufactured by 3Shape®.

The scanner 150 may be used to perform an intraoral scan of a patient's oral cavity. An intraoral scan application 108 running on computing device 105 may communicate with the scanner 150 to effectuate the intraoral scan. A result of the intraoral scan may be a sequence of intraoral images that have been discretely generated (e.g., by pressing on a "generate image" button of the scanner for each image). Alternatively, a result of the intraoral scan may be one or more videos of the patient's oral cavity. An operator may start recording the video with the scanner 150 at a first position in the oral cavity, move the scanner 150 within the oral cavity to a second position while the video is being taken, and then stop recording the video. In some embodiments, recording may start automatically as the scanner identifies either teeth or soft tissue from the oral cavity. The scanner 150 may transmit the discrete intraoral images or intraoral video (referred to collectively as intraoral image data 135) to the computing device 105. Computing device 105 may store the image data 135 in data store 110. Alternatively, scanner 150 may be connected to another system that stores the image data in data store 110. In such an embodiment, scanner 150 may not be connected to computing device 105.

According to an example, a user (e.g., a practitioner) may subject a patient to intraoral scanning. In doing so, the user may apply scanner 150 to one or more patient intraoral locations. The scanning may be divided into one or more segments. As an example the segments may include a lower buccal region of the patient, a lower lingual region of the patient, a upper buccal region of the patient, an upper lingual region of the patient, one or more preparation teeth of the patient (e.g., teeth of the patient to which a dental device such as a crown or an orthodontic alignment device will be applied), one or more teeth which are contacts of preparation teeth (e.g., teeth not themselves subject to a dental device but which are located next to one or more such teeth or which interface with one or more such teeth upon mouth closure), and/or patient bite (e.g., scanning performed with closure of the patient's mouth with scan being directed towards an interface area of the patient's upper and lower teeth). Via such scanner application, the scanner 150 may provide image data (also referred to as scan data) 135 to computing device 105. The image data 135 may include 2D intraoral images and/or 3D intraoral images. Such images may be provided from the scanner to the computing device 105 in the form of one or more points (e.g., one or more pixels and/or groups of pixels). For instance, the scanner 150 may provide such a 3D image as one or more point clouds.

The manner in which the oral cavity of a patient is to be scanned may depend on the procedure to be applied thereto. For example, if an upper or lower orthodontic appliance is to be created, then a full scan of the mandibular or maxillary edentulous arches may be performed. In contrast, if a bridge is to be created, then just a portion of a total arch may be scanned which includes an edentulous region, the neighboring abutment teeth and the opposing arch and dentition. Thus, the dental practitioner may input the identity of a procedure to be performed into intraoral scan application 108. For this purpose, the dental practitioner may choose the procedure from a number of preset options on a drop-down menu or the like, from icons or via any other suitable graphical input interface. Alternatively, the identity of the procedure may be input in any other suitable way, for example by means of preset code, notation or any other suitable manner, intraoral scan application 108 having been suitably programmed to recognize the choice made by the user.

By way of non-limiting example, dental procedures may be broadly divided into prosthodontic (restorative) and orthodontic procedures, and then further subdivided into specific forms of these procedures. Additionally, dental procedures may include identification and treatment of gum disease, sleep apnea, and intraoral conditions. The term prosthodontic procedure refers, inter alia, to any procedure involving the oral cavity and directed to the design, manufacture or installation of a dental prosthesis at a dental site within the oral cavity, or a real or virtual model thereof, or directed to the design and preparation of the dental site to receive such a prosthesis. A prosthesis may include any restoration such as crowns, veneers, inlays, onlays, and bridges, for example, and any other artificial partial or complete denture. The term orthodontic procedure refers, inter aha, to any procedure involving the oral cavity and directed to the design, manufacture or installation of orthodontic elements at a dental site within the oral cavity, or a real or virtual model thereof, or directed to the design and preparation of the dental site to receive such orthodontic elements. These elements may be appliances including but not limited to brackets and wires, retainers, clear aligners, or functional appliances.

A type of scanner to be used may also be input into intraoral scan application 108, typically by a dental practitioner choosing one among a plurality of options. Examples of scanners that may be used include wand scanners, tray scanners, and so on. If the scanner 150 that is being used is not recognizable by intraoral scan application 108, it may nevertheless be possible to input operating parameters of the scanner thereto instead. For example, the optimal spacing between a head of the scanner and scanned surface can be provided, as well as the capture area (and shape thereof) of the dental surface capable of being scanned at this distance. Alternatively, other suitable scanning parameters may be provided.

Intraoral scan application 108 may identify spatial relationships that are suitable for scanning the dental site so that complete and accurate image data may be obtained for the procedure in question. Intraoral scan application 108 may establish an optimal manner for scanning a target area of the dental site.

Intraoral scan application 108 may identify or determine a scanning protocol by relating the type of scanner, resolution thereof, capture area at an optimal spacing between the scanner head and the dental surface to the target area, etc. For a point-and-shoot scanning mode, the scanning protocol may include a series of scanning stations spatially associated with the dental surfaces of the target area. Preferably, overlapping of the images or scans capable of being obtained at adjacent scanning stations is designed into the scanning protocol to enable accurate image registration, so that intraoral images can be registered to provide a composite 3D virtual model. For a continuous scanning mode (video scan), scanning stations may not be identified. Instead, a practitioner may activate the scanner and proceed to move the scanner within the oral cavity to capture a video of the target area from multiple different viewpoints.

In one embodiment, intraoral scan application 108 includes an image registration module 111, a historical template module 112, an area of interest (AOI) identifying module 115, a flagging module 118 and a model generation module 125. Alternatively, the operations of one or more of the image registration module 111, historical template module 112, AOI identifying module 115, flagging module 118 and/or model generation module 125 may be combined into a single module and/or divided into multiple modules.

Image registration module 111 is responsible for registering or stitching together images received during a scan session. The images may include X-rays, 2D intraoral images, 3D intraoral images, 2D models, and/or virtual 3D models corresponding to the patient visit during which the scanning occurs. In one embodiment, performing image registration includes capturing 3D data of various points of a surface in multiple images (views from a camera), and registering the images by computing transformations between the images. The images may then be integrated into a common reference frame by applying appropriate transformations to points of each registered image. In one embodiment, the images may be registered together in real time, during the current scan session.

In one embodiment, as each new image is received, that new image is compared to some or all previous images received during a current scan session. If there is sufficient overlap between the current image and one or more of the previous images, then the current image may be registered with those one or more previous images. Image registration algorithms are carried out to register intraoral images, which essentially involves determination of the transformations which align one image with another image. Image registration may involve identifying multiple points in each image (e.g., point clouds) of an image pair, surface fitting to the points of each image, and using local searches around points to match points of the two adjacent images. For example, image registration module 111 may match points of one image with the closest points interpolated on the surface of the other image, and iteratively minimize the distance between matched points. Image registration module 111 may also find the best match of curvature features at points of one image with curvature features at points interpolated on the surface of the other image, without iteration. Image registration module 111 may also find the best match of spin-image point features at points of one image with spin-image point features at points interpolated on the surface of the other image, without iteration. Other techniques that may be used for image registration include those based on determining point-to-point correspondences using other features and minimization of point-to-surface distances, for example. Other image registration techniques may also be used.

Many image registration algorithms perform the fitting of a surface to the points in adjacent images, which can be done in numerous ways. Parametric surfaces such as Bezier and B-Spline surfaces are most common, although others may be used. A single surface patch may be fit to all points of an image, or alternatively, separate surface patches may be fit to any number of a subset of points of the image. Separate surface patches may be fit to have common boundaries or they may be fit to overlap. Surfaces or surface patches may be fit to interpolate multiple points by using a control-point net having the same number of points as a grid of points being fit, or the surface may approximate the points by using a control-point net which has fewer number of control points than the grid of points being fit. Various matching techniques may also be employed by the image registration algorithms.

In one embodiment, image registration module 111 may determine a point match between images, which may take the form of a two dimensional (2D) curvature array. A local search for a matching point feature in a corresponding surface patch of an adjacent image is carried out by computing features at points sampled in a region surrounding the parametrically similar point. Once corresponding point sets are determined between surface patches of the two images, determination of the transformation between the two sets of corresponding points in two coordinate frames can be solved. Essentially, an image registration algorithm may compute a transformation between two adjacent images that will minimize the distances between points on one surface, and the closest points to them found in the interpolated region on the other image surface used as a reference. Each transformation may include rotations about one to three axes and translations within one to three planes.

In some instances, a received image may not be registerable with any other image from a current scan session. In traditional systems such images would be discarded, and a user would be asked to rescan one or more areas. Embodiments of the present invention enable such images that do not register to other images from a scan session by comparing and registering such images to a historical template that has been generated from scan data collected in a previous scan session.

Historical template module 112 is responsible for determining that historical scans exist for a particular patient and registering images of a current scan session to a historical template based on overlapping data from the images and the historical scan data. The past historical templates may be or include X-rays, 2D intraoral images, 3D intraoral images, 2D models, and/or virtual 3D models of the patient corresponding to past visits of the patient and/or to dental records of the patient. The past historical templates are included in reference data 138 for the patient.

In one embodiment, historical template module 112 may receive an indication from computing device 105 that a current image of an intraoral scan session cannot or should not be registered to any other images of the current session. Registering may be improper when the current image does not adequately overlap any other existing image of the current scan. In this example, historical template module 112 may determine that the images of the current scan are related to historical image data for the same patient. Historical image data may include historical templates for the patient; each template relating to a previous image scan session for the patient. In one example, a patient may have undergone an intraoral scan once a month for the last 12 months, in which case 12 historical templates for the patient would be available. Historical template module 112 may determine that the images of the current scan are associated with the historical templates and map the current images of the current scan session to one of the historical templates (e.g., the most recent template). In another embodiment, a user may select a historical template to which the current scan session images should map.

AOI identifying module 115 is responsible for identifying areas of interest (AOIs) from intraoral scan data (e.g., intraoral images) and/or virtual 3D models generated from intraoral scan data. In one embodiment, areas of interest are determined by comparing images of a current scan session to a historical template to determine any differences. Such areas of interest may include voids (e.g., areas for which scan data is missing), areas of conflict or flawed scan data (e.g., areas for which overlapping surfaces of multiple intraoral images fail to match), areas indicative of foreign objects (e.g., studs, bridges, etc.), areas indicative of tooth wear, areas indicative of tooth decay, areas indicative of receding gums, unclear gum line, unclear patient bite, unclear margin line (e.g., margin line of one or more preparation teeth), and so forth. An identified void may be a void in a surface of an image. Examples of surface conflict include double incisor edge and/or other physiologically unlikely tooth edge, and/or bite line shift. The AOI identifying module 115 may, in identifying an AOI, analyze patient image data 135 including historical templates (e.g., historical 3D image point clouds) and/or one or more virtual 3D models of the patient alone and/or relative to reference data 138. The analysis may involve direct analysis (e.g., pixel-based and/or other point-based analysis), the application of machine learning, and/or the application of image recognition. AOI identifying module 115 may additionally or alternatively analyze patient scan data relative to reference data in the form of dental record data of the patient and/or data of the patient from prior to the patient visit (e.g., historical templates including one or more prior-to-the-visit 3D image point clouds and/or one or more prior-to-the-visit virtual 3D models of the patient).

In an example, AOI identifying module 115 may generate a first historical template of a dental site based on a first scan session of the dental site taken at a first time and later generate a second virtual model of the dental site based on a second scan session of the dental site taken at a second time. The AOI identifying module 115 may then compare the first historical template to the second virtual model to determine a change in the dental site and identify an AOI to represent the change.

Identifying of areas of interest concerning missing and/or flawed scan data may involve the AOI identifying module 115 performing direct analysis, for instance determining one or more pixels or other points to be missing from patient scan data and/or one or more virtual 3D models of the patient. Flagging module 118 is responsible for determining how to present and/or call out the identified areas of interest. Flagging module 118 may provide indications or indicators regarding scan assistance, diagnostic assistance, and/or foreign object recognition assistance. Areas of interest may be determined, and indicators of the areas of interest may be provided, during and/or after an intraoral scan session. Such indications may be provided prior to and/or without construction of an intraoral virtual 3D model. Alternatively, indications may be provided after constructions of an intraoral virtual 3D model of a dental site.

Examples of the flagging module 118 providing indications regarding scan assistance, diagnostic assistance, and/or foreign object recognition assistance will now be discussed. The flagging module 118 may provide the indications during and/or after an intraoral scan session. The indications may be presented (e.g., via a user interface) to a user (e.g., a practitioner) in connection with and/or apart from one or more depictions of teeth and/or gingivae of a patient (e.g., in connection with one or more X-rays, 2D intraoral images, 3D intraoral images, 2D models, and/or virtual 3D models of the patient). Indication presentation in connection with depictions of patient teeth and/or gingivae may involve the indications being placed so as to correlate an indication with the corresponding portion of the teeth and/or gingivae. As an illustration, a diagnostic assistance indication regarding a broken tooth might be placed so as to identify the broken tooth.

The indications may be provided in the form of flags, markings, contours, text, images, and/or sounds (e.g., in the form of speech). Such a contour may be placed (e.g., via contour fitting) so as to follow an extant tooth contour and/or gingival contour. As an illustration, a contour corresponding to a tooth wear diagnostic assistance indication may be placed so as to follow a contour of the worn tooth. Such a contour may be placed (e.g., via contour extrapolation) with respect to a missing tooth contour and/or gingival contour so as to follow a projected path of the missing contour. As an illustration, a contour corresponding to missing tooth scan data may be placed so as to follow the projected path of the tooth portion which is missing, or a contour corresponding to missing gingival scan data may be placed so as to follow the projected path of the gingival portion which is missing.

In presenting indications (e.g., flags), the flagging module 118 may perform one or more operations to pursue proper indication display. For instance, where indications are displayed in connection with one or more depictions of teeth and/or gingivae (e.g., a corresponding virtual 3D model), such operations may act to display a single indication rather than, say, multiple indications for a single AOI. Additionally, processing logic may select a location in 3D space for indication placement.

Where indications are displayed in connection with a 3D teeth and/or gingiva depiction (e.g., in connection with a virtual 3D model), the flagging module 118 may divide the 3D space into cubes (e.g., voxels corresponding to one or more pixels of the 3D space). The flagging module 118 may then consider the voxels relative to the voxels of determined AOIs and tag voxels so as to indicate the indications (e.g., flags) to which they correspond.

Where more than one cube is tagged with respect to a given one of the indications, the flagging module 118 may act such that only one of the tagged voxels receives flag placement. Moreover, the flagging module 118 may choose a particular voxel which it determines will provide for ease of viewing by the user. For instance, such choice of a voxel may take into account the totality of indications to be flagged and may endeavor to avoid crowding a single cube with multiple flags where such can be avoided.

In placing indications (e.g., flags) the flagging module 118 may or may not take into account factors other than seeking to avoid crowding. For instance, the flagging module 118 may take into account available lighting, available angle, available zoom, available axes of rotation, and/or other factors corresponding to user viewing of the teeth and/or gingiva depiction (e.g., the virtual 3D model), and may seek indication (e.g., flag) placement which seeks to optimize user viewing in view of these factors).

The flagging module 118 may key the indications (e.g., via color, symbol, icon, size, text, and/or number). The keying of an indication may serve to convey information about that indication. The conveyed information may include classification of an AOI, a size of an AOI and/or an importance rank of an AOI. Accordingly, different flags or indicators may be used to identify different types of AOIs. For example, pink indicators may be used to indicate gingival recession and white indicators may be used to indicate tooth wear. Flagging module 118 may determine a classification, size and/or importance rank of an AOI, and may then determine a color, symbol, icon, text, etc. for an indicator of that AOI based on the classification, size and/or importance rank.

Turning to keying which conveys AOI classification, indicators may identify classifications assigned to intraoral areas of interest. For examples, AOIs may be classified as voids, changes, conflicts, foreign objects, or other types of AOI. AOIs representing changes in patient dentition may represent tooth decay, receding gums, tooth wear, a broken tooth, gum disease, gum color, moles, lesions, tooth shade, tooth color, an improvement in orthodontic alignment, degradation in orthodontic alignment, and so on. Different criteria may be used for identifying each such class of AOI. For example, a void may be identified by lack of image data, a conflict may be identified by conflicting surfaces in image data, changes may be identified based on differences in image data, and so on.

When a scan session is in progress or when the scan is complete (e.g., all images for a dental site have been captured), model generation module 125 may generate a virtual 3D model of the scanned dental site. During a scan session, model generation module 125 may use the image registration data output by image registration module 111 to generate a three dimensional representation of the dental site. The three dimensional representation may additionally include image registration data output by historical template module 112 (e.g., registration of current images to a historical template). AOI identifying module 115 and/or flagging module 118 may perform operations to identify AOIs and/or to indicate such AOIs in the three dimensional representation.

Model generation module 125 may integrate all images into a single virtual 3D model by applying the appropriate determined transformations to each of the images. In one embodiment, model generation module 125 may determine that a historical template associated with the current scan session includes areas not yet scanned in a current scan session. In such a case, model generation module 125 may use data from the historical template, to supplement the data of the current scan. For example, if there are any regions that have not yet been scanned in a current scan session, a data from a historical template may be used to fill in the missing regions. In one embodiment, the data from the historical template is shown using a different visualization than the data from the images received during the current scan session. For example, surfaces associated with images from the current scan session may be shown as solid objects, and surfaces associated with the historical template may be shown as translucent objects a pixelated objects.

Figure 2A:
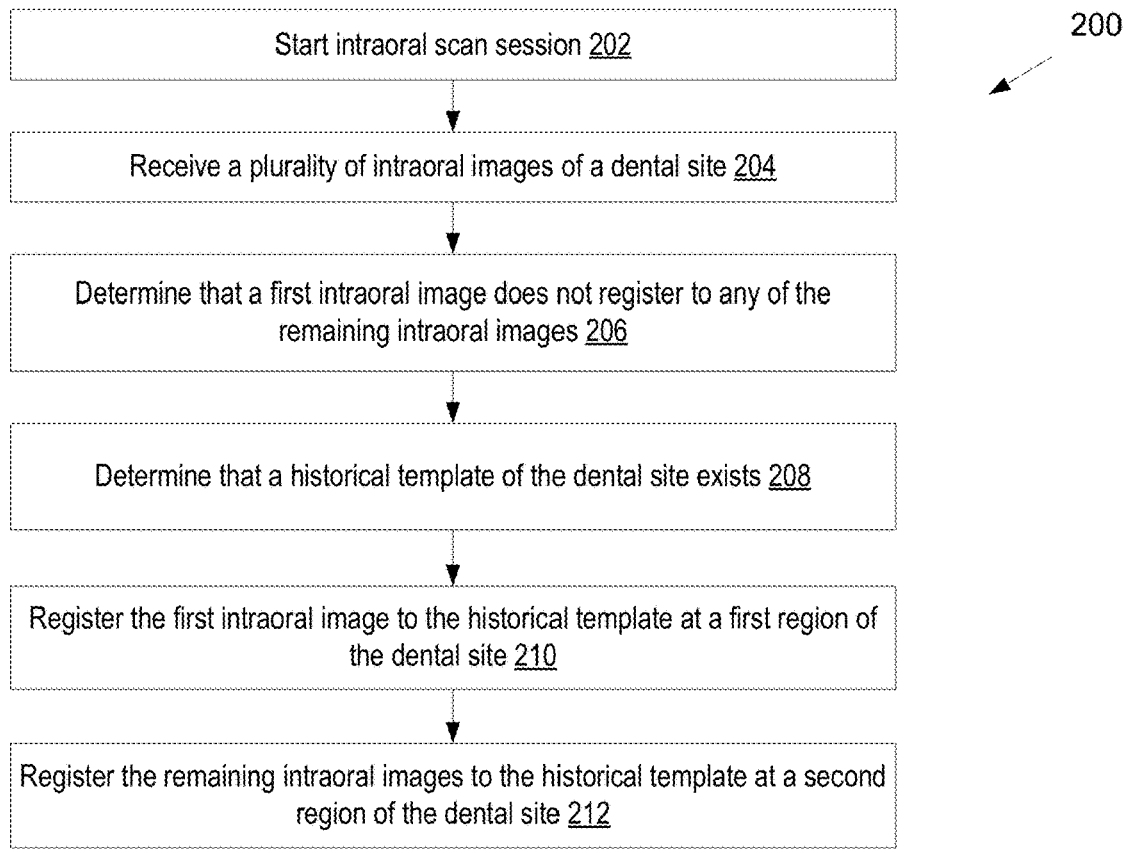
FIG. 2A illustrates a flow diagram for a first method of referencing a historical scan during an intraoral scan session, in accordance with embodiments of the present invention.

FIG. 2A illustrates a flow diagram for a first method 200 of referencing a historical scan during an intraoral scan session, in accordance with embodiments of the present invention. This method may be performed by processing logic that comprises hardware (e.g., circuitry, dedicated logic, programmable logic, microcode, etc.), software (such as instructions run on a processing device), or a combination thereof. In one embodiment, processing logic corresponds to computing device 105 of FIG. 1 (e.g., to a computing device 105 executing an intraoral scan application 108).

At block 202 of method 200, an intraoral scan session of a dental site is started by a dental practitioner. The scan session may be for an intraoral scan of a partial or full mandibular or maxillary arch, or a partial or full scan of both arches. The dental practitioner may move an intraoral scanner to a first intraoral position and generate a first intraoral image. At block 204, processing logic receives a plurality of intraoral images. The intraoral images may be discrete images (e.g., taken from a point-and-shoot mode) or frames of an intraoral video (e.g., taken in a continuous scanning or video mode). The intraoral images may be three dimensional (3D) images having a particular height, width and depth.

At block 206, processing logic determines that one or more of the intraoral images of the current scan session does not register to any already existing images associated with the current scan session. In one embodiment, images of the scan session may not register to existing images when they do not sufficiency overlap each other. Images do not sufficiently overlap each other when there is insufficient overlapping data between the two images to be able to determine that a portion of the first image is of the same object (e.g., region of a dental site) as a portion of the second image. When images do not sufficiently overlap each other, registration may be less accurate or may not be possible. Images may be registered when a sufficient area and/or number of points within each image may be mapped to an adjacent image. In one embodiment, images whose overlapping area and/or number of overlapping points do not meet a predetermined threshold may not be registered.

In one embodiment, when an intraoral image of a current scan session is not registered to any other image of the current scan session, processing logic at block 208 may determine that the images of the current scan session are associated with an existing historical template. The historical template may be a three dimensional virtual model of a dental site as generated from images taken during a previous scan session. The historical template may have been generated after stitching together the images taken during the previous scan session. Alternatively, processing logic may determine that scan data exists from previous scan sessions, but no historical template may have been generated. In such an instance, processing logic may generate a historical template from the previous scan data. In one embodiment, processing logic may search a database to identify historical templates associated with images of the current scan session or with the current patient. Current session images may be compared to previously captured images to determine whether they are associated. In another embodiment, scan sessions are associated by virtue of the fact that they are associated with the same patient in a database. A user may also manually identify stored historical templates for a patient and associate them with the current scan session.

At block 210, processing logic may determine the position of the first image of the current scan session with respect to the historical template and register the image to the template. In one embodiment, the remaining images of the current scan session at a second region of the dental site may be registered to the historical template at a first region of the dental site (see block 212). In one embodiment, images are registered to the historical template using a first set of criteria, whereas images are registered to each other using a second set of criteria. In one embodiment, the first set of criteria is less restrictive than the second set. In one embodiment, images may be registered to a historical template under the less restrictive criteria when they may not be registered to other images under the stricter criteria.

Accordingly, image data from the historical template may be provided to a user with associated images from the current scan session overlaid in position over the historical template. Alternatively, the historical template may not be provided to a user and the images of the current scan session are provided to the user placed on an invisible historical template. Images of the current scan session that are not registered to other images of the current scan session may still be registered to the historical template. Unregistered images of the current scan session, despite not having sufficient overlap to register to current scan session images, may have sufficient overlap with areas of the historical template to allow placement onto the historical template. Determining proper placement of an unregistered image based on the historical template allows unregistered images to be registered to other images of a current scan session, despite insufficient overlap with those images. In one embodiment, processing logic may utilize the same techniques discussed above with respect to registering images to determine placement of an image with respect to a historical template.

In one embodiment, processing logic may generate a three dimensional virtual model of the dental site from the intraoral images. Processing logic may determine that a portion of the intraoral images represents soft tissue (e.g., gums) based at least in part on a difference between a previous depiction of the dental site as represented in the historical template and a current depiction of the dental site as represented in the intraoral images. The portion of the intraoral images determined to represent the soft tissue may be removed from the three dimensional virtual model of the dental site.

In another embodiment, processing logic of method 200 may identify a restorative area of the dental site represented in the plurality of intraoral images. The restorative area may include a stump (e.g., a preparation) of a tooth. Processing logic may also determine a baseline area that represents a surface of the tooth before the tooth was ground into the stump based on the historical template and provide the baseline area to be displayed in a graphical user interface.

Figure 2B:
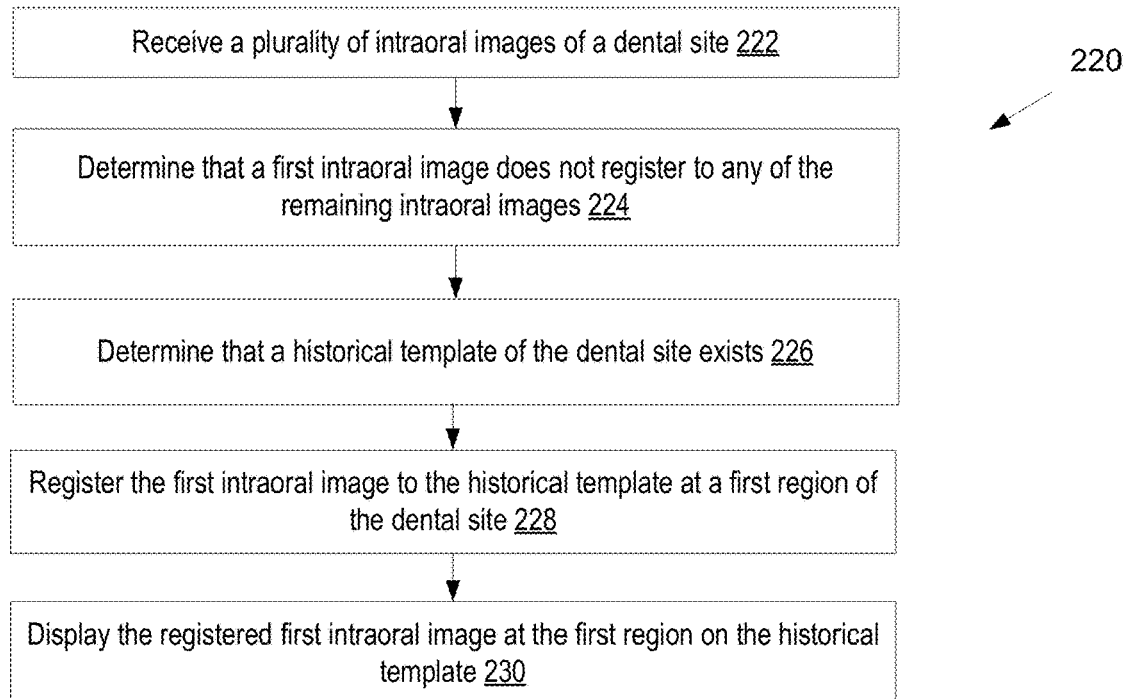
FIG. 2B illustrates a flow diagram for a second method of referencing a historical scan during an intraoral scan session, in accordance with embodiments of the present invention.

FIG. 2B illustrates a flow diagram for a second method 220 of referencing a historical scan during an intraoral scan session, in accordance with embodiments of the present invention. This method may be performed by processing logic that comprises hardware (e.g., circuitry, dedicated logic, programmable logic, microcode, etc.), software (such as instructions run on a processing device), or a combination thereof. The first method 200 and second method 220 may be performed together or separately in embodiments. In one embodiment, processing logic corresponds to computing device 105 of FIG. 1 (e.g., to a computing device 105 executing an intraoral scan application 108).

At block 222 of method 220, processing logic receives a plurality of intraoral images during a intraoral scan session. The intraoral images may be discrete images (e.g., taken from a point-and-shoot mode) or frames of an intraoral video (e.g., taken in a continuous scanning or video mode). The intraoral images may be three dimensional (3D) images having a particular height, width and depth.

At block 224, processing logic determines that one or more of the intraoral images of the current scan session does not register to any already existing images associated with the current scan session. In one embodiment, images of the scan session may not register to existing images when they do not sufficiency overlap each other. Images do not sufficiently overlap each other when there is insufficient overlapping data between the two images to be able to determine that a portion of the first image is of the same object (e.g., region of a dental site) as a portion of the second image. When images do not sufficiently overlap each other, registration may be less accurate or may not be possible. Images may be registered when a sufficient area and/or number of points within each image may be mapped to an adjacent image. In one embodiment, images whose overlapping area and/or number of overlapping points do not meet a predetermined threshold may not be registered.

In one embodiment, when an intraoral image of a current scan session is not registered to any other image of the current scan session, processing logic at block 226 may determine that the images of the current scan session are associated with an existing historical template. The historical template may be a three dimensional virtual model of a dental site as generated from images taken during a previous scan session. The historical template may have been generated after stitching together the images taken during the previous scan session. Alternatively, processing logic may determine that scan data exists from previous scan sessions, but no historical template may have been generated. In such an instance, processing logic may generate a historical template from the previous scan data. In one embodiment, processing logic may search a database to identify historical templates associated with images of the current scan session or with the current patient. Current session images may be compared to previously captured images to determine whether they are associated. In another embodiment, scan sessions are associated by virtue of the fact that they are associated with the same patient in a database. A user may also manually identify stored historical templates for a patient and associate them with the current scan session.

At block 228, processing logic may determine the position of the first image of the current scan session with respect to the historical template and register the image to the template. In one embodiment, the remaining images of the current scan session at a second region of the dental site may be registered to the historical template at a first region of the dental site.

At block 230, processing logic may display the registered first intraoral image at the first region on the historical template. In another embodiment, processing logic may display additional images on a second region of the historical template. Accordingly, image data from the historical template may be provided to a user with associated images from the current scan session overlaid in position over the historical template. Alternatively, the historical template may not be provided to a user and the images of the current scan session are provided to the user placed on an invisible historical template. Images of the current scan session that are not registered to other images of the current scan session may still be registered to the historical template. Unregistered images of the current scan session, despite not having sufficient overlap to register to current scan session images, may have sufficient overlap with areas of the historical template to allow placement onto the historical template. Determining proper placement of an unregistered image based on the historical template allows unregistered images to be registered to other images of a current scan session, despite insufficient overlap with those images. In one embodiment, processing logic may utilize the same techniques discussed above with respect to registering images to determine placement of an image with respect to a historical template.

In one embodiment, processing logic may generate a three dimensional virtual model of the dental site from the intraoral images. Processing logic may determine that a portion of the intraoral images represents soft tissue (e.g., gums) based at least in part on a difference between a previous depiction of the dental site as represented in the historical template and a current depiction of the dental site as represented in the intraoral images. The portion of the intraoral images determined to represent the soft tissue may be removed from the three dimensional virtual model of the dental site.

In another embodiment, processing logic of method 220 may identify a restorative area of the dental site represented in the plurality of intraoral images. The restorative area may include a stump (e.g., a preparation) of a tooth. Processing logic may also determine a baseline area that represents a surface of the tooth before the tooth was ground into the stump based on the historical template and provide the baseline area to be displayed in a graphical user interface.

Figure 3A:
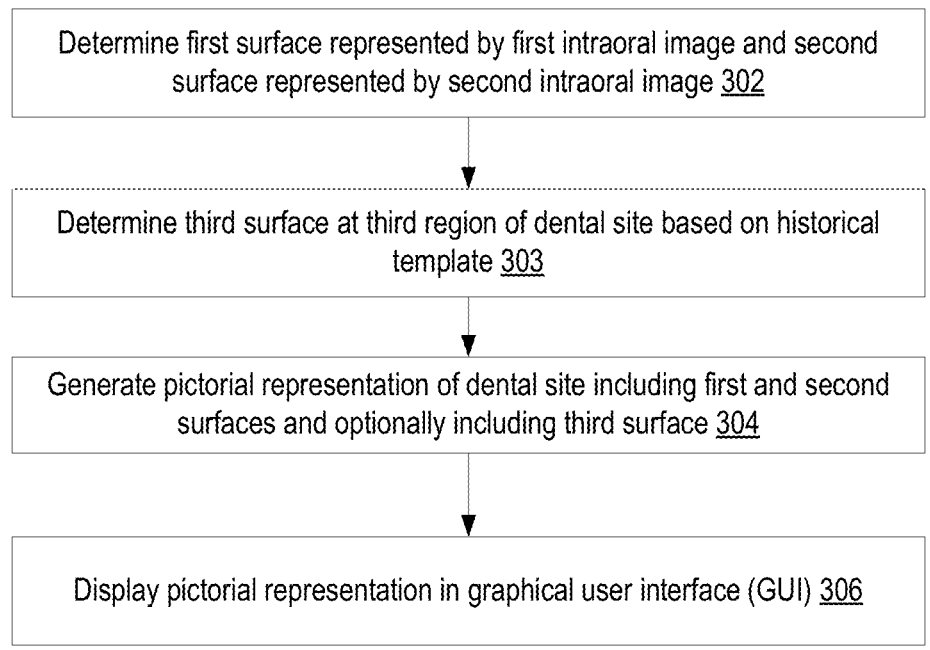
FIG. 3A illustrates a flow diagram for a method of generating a surface of an intraoral scan session, in accordance with embodiments of the present invention.

FIG. 3A illustrates a flow diagram for a method 300 of generating a surface of a dental site during an intraoral scan session, in accordance with embodiments of the present invention. This method may be performed by processing logic that comprises hardware (e.g., circuitry, dedicated logic, programmable logic, microcode, etc.), software (such as instructions run on a processing device), or a combination thereof. In one embodiment, processing logic corresponds to computing device 105 of FIG. 1 (e.g., to a computing device 105 executing an intraoral scan application 108). In one embodiment, method 300 continues from block 212 of method 200.

At block 302 of method 300, processing logic may determine a first surface represented by a first intraoral image and a second surface represented by a second intraoral image. The first surface may be associated with a first region of a dental site and the second surface may be associated with a second region of the dental site that is separated from the first surface of the dental site. At block 303, processing logic may determine a third surface and/or additional surfaces at additional regions of the dental site based on a historical template. The third region may separate the first region and the second region.

At block 304, processing logic generates a pictorial representation of the dental site that includes the first surface and the second surface. In one embodiment, the pictorial representation may include a transformed representation of the first intraoral image (e.g., that has been rotated, translated and/or scaled) at the first region (determined in block 206 of FIG. 2A) and transformed representations of the remaining intraoral images in the second region (see block 212). The transformed first intraoral image may define a first surface of the dental site and the transformed remaining intraoral images may define a second surface of the dental site. The pictorial representation may optionally also include the third surface and/or any additional surfaces generated from the historical template. At block 306, processing logic may display the pictorial representation in a graphical user interface (GUI) or may output the pictorial representation for display on a GUI.

One or more additional images including the third region may be received by processing logic and registered to the first intraoral image of the first region and one or more of the remaining intraoral images of the second region. The one or more additional images may then be used to redraw the third surface based on current patient data.

Figure 3B:
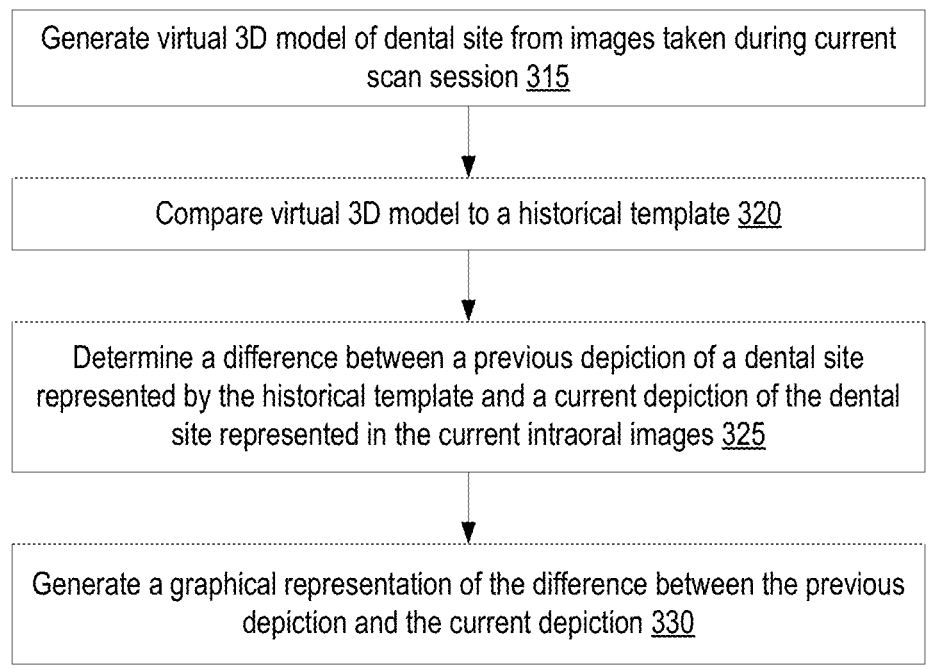
FIG. 3B illustrates a flow diagram for a method of determining a depiction of a change to a dental site between a current intraoral scan session and a past intraoral scan session, in accordance with embodiments of the present invention.

FIG. 3B illustrates a flow diagram for a method 310 of determining a change to a dental site between a current intraoral scan session and a past intraoral scan session, in accordance with embodiments of the present invention. This method may be performed by processing logic that comprises hardware (e.g., circuitry, dedicated logic, programmable logic, microcode, etc.), software (such as instructions run on a processing device), or a combination thereof. In one embodiment, processing logic corresponds to computing device 105 of FIG. 1 (e.g., to a computing device 105 executing an intraoral scan application 108).

At block 315 of method 310, processing logic may generate a virtual 3D model of a dental site from images taken during a current scan session. The virtual 3D model may be generated by registering and stitching together the images. At block 320, processing logic compares the virtual 3D model to a historical template generated from images associated with a previous scan of the dental site at an earlier time. The historical template may be another virtual 3D model of the dental site that was generated from images taken during a previous scan session. For example, a dental practitioner may perform scans of a patient's dentition on an annual basis. Processing logic may compare the current state of the patient's dental site to the state of the patient's dental site that is a year old. In additional embodiments, multiple historical templates may be available for a patient, which may be based on images taken at different time periods. A dental practitioner may select which historical template to compare the virtual 3D model to.

At block 325, processing logic determines a difference between a previous depiction of the dental site as represented it the historical template and a current depiction of the dental site as represented in the virtual 3D model generated from the plurality of intraoral images of the current scan.

To compare a virtual 3D model of a current scan session to a historical template and determine differences there between, processing logic determines an alignment between the virtual 3D model (or images used to generate the virtual 3D model) and the historical template based on geometric features shared by the virtual 3D model and the historical template. This comparison may identify areas of interest such as tooth wear, cavities, and so forth.

At block 330, processing logic provides graphical representation of the difference between the current depiction of the dental site and the previous depiction of the dental site as represented in the historical template. In one embodiment, processing logic compares the virtual 3D model to multiple historical templates, and may additionally compare the historical templates to one another. Processing logic may then generate a moving image (e.g., a video) showing a change to the dental site over time. For example, a time lapse video may be generated that shows gradual wearing of a patient's teeth, yellowing of the teeth, receding gum lines, and so on.

The differences between the current and previous depiction of the dental site may be identified as one type of area of interest. In other embodiments, other types of areas of interest may be provided. For example, the provided area of interest may include a region of the dental site that is represented in the historical template but not represented in the intraoral images of the current scan. In one embodiment, processing logic interpolates a shape for the intraoral area of interest based on geometric features surrounding the intraoral area of interest and/or based on geometric features of the intraoral area of interest (if such features exist). For example, if the intraoral area of interest is a void, then the regions around the void may be used to interpolate a surface shape of the void. The shape of the intraoral area of interest may be displayed in manner to contrast the intraoral area of interest from surrounding imagery. For example, teeth may be shown in white, while the intraoral area of interest may be shown in red, black, blue, green, or another color. Additionally or alternatively, an indicator such as a flag may be used as an indication of the intraoral area of interest. The indicator may be remote from the intraoral area of interest but include a pointer to the intraoral area of interest. The intraoral area of interest may be hidden or occluded in many views of the dental site. However, the indicator may be visible in all or many such views. For example, the indicator may be visible in all views of the scanned dental site unless the indicator is disabled. The provided indications of the intraoral areas of interest may be displayed while the intraoral scan session is ongoing.

Figure 4:
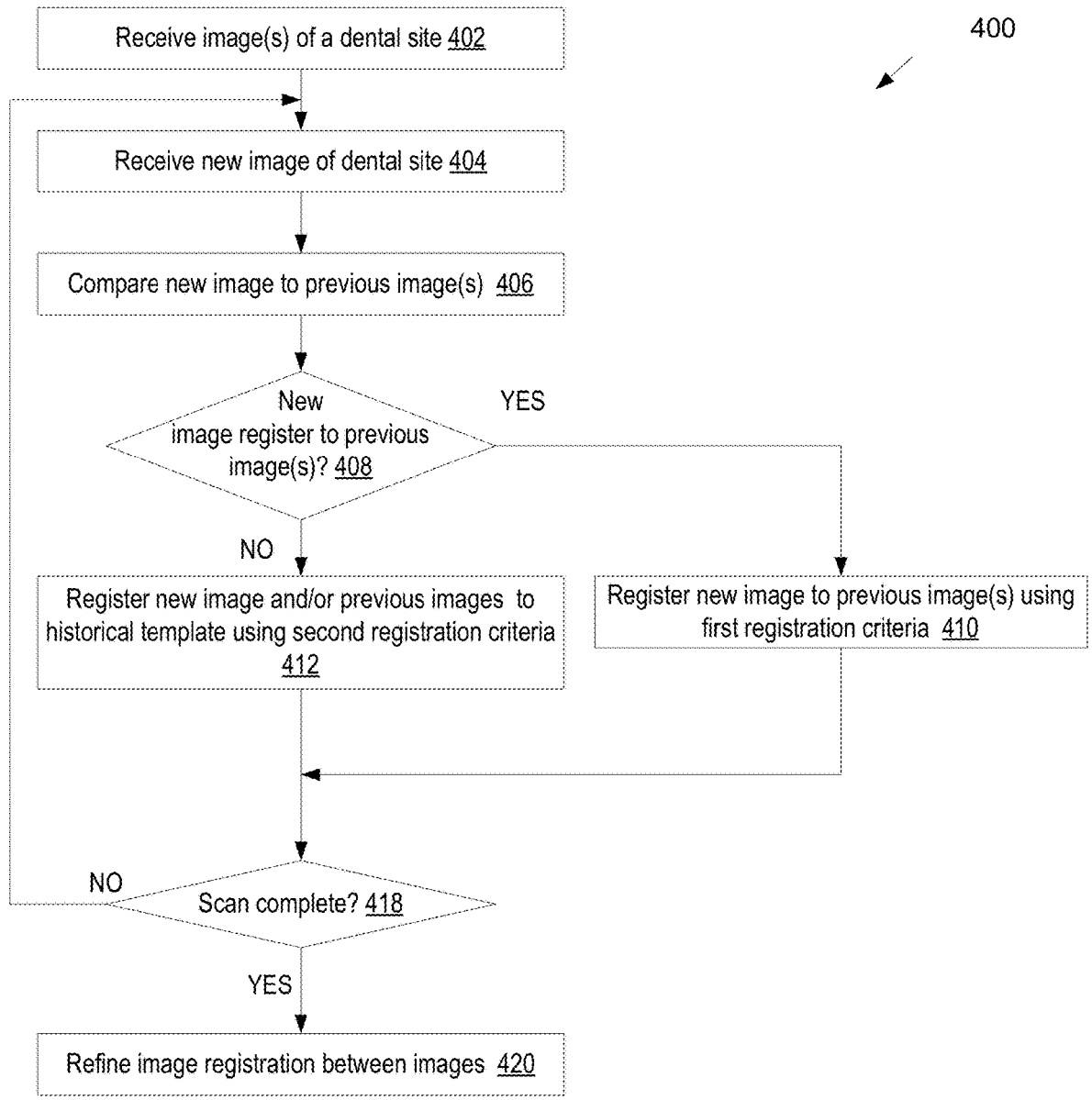
FIG. 4 illustrates a flow diagram for another method of referencing a historical scan during an intraoral scan session, in accordance with embodiments of the present invention.

FIG. 4 illustrates a flow diagram for another method 400 of referencing a historical scan during an intraoral scan session, in accordance with embodiments of the present invention. This method may be performed by processing logic that comprises hardware (e.g., circuitry, dedicated logic, programmable logic, microcode, etc.), software (such as instructions run on a processing device), or a combination thereof. In one embodiment, processing logic corresponds to computing device 105 of FIG. 1 (e.g., to a computing device 105 executing an intraoral scan application 108).

At block 402 of method 400, processing logic receives one or more images of a dental site. Processing logic may perform image registration to stitch these images together if multiple images are received. As the images are stitched together, a virtual 3D model of the dental site that includes the stitched together images may be generated and displayed.

At block 404, processing logic receives a new image of the dental site. At block 406, processing logic compares the new image to some or all of the previous images. At block 408, processing logic determines whether the new image can be registered to any of the previous images. The new image can be registered to a previous image if first registration criteria are satisfied. The first registration criteria may include a threshold number of curves, edges, point and/or other features of the new image that match curves, edges, points and/or other features of a previous image. A match for a feature may be determined when the feature of the new image deviates from the feature of the previous image by less than a deviation threshold, such as 10%. Collectively, the number of matching features and the degree of match may be referred to herein as an amount of overlap. Accordingly, images may be registerable if the amount of overlap between those two images satisfies an overlap threshold. If there are an insufficient number of features in the new image that match features of any previous image (amount of overlap is less than an overlap threshold), then registration cannot be performed and the method proceeds to block 412. If there are a sufficient number of features in the new image that match features of at least one previous image (amount of overlap meets or exceeds the overlap threshold), then the method continues to block 410.

At block 410, processing logic registers the new image to one or more of the previous images using the first registration criteria. Processing logic may then update the 3D model of the dental site to include the new image stitched to the previous images and display the updated 3D model.

At block 412, processing logic registers the new image to a historical template using second image registration criteria. At block 412 processing logic may also register the previous images to the historical template if the previous images have not already been registered to the historical template. The historical template may be a virtual 3D model of the patient's dental site that was generated based on images taken at a previous time. The second registration criteria may be less restrictive than the first registration criteria. For example, a patient's dental site may change over time. Teeth may become slightly worn and change shape, teeth may move slightly, and so forth. Accordingly, images of the same tooth may not match perfectly. To account for these changes over time and still enable a current image to register to images and/or a virtual model generated from images taken at a previous time, the registration criteria are relaxed. The relaxed registration criteria may include a reduction in the threshold number of features that are specified to register two images and/or an increase in the amount of deviation that is permitted for recognition of a match between two features.

Registration of the new image and the previous images to the historical template enables processing logic to determine the regions of the dental site represented by the new image and the previous images. Accordingly, once the new image and the previous images have been registered, the relative positions of the new image and the previous images can be determined. Processing logic may update the 3D model of the dental site based on the registration to the historical template. As a result, the 3D model may show a first region of the dental site represented by the previous images that have been stitched together and may show a second region of the dental site represented by the new image. There may be a small or large separation between the first region and the second region. For regions of the dental site for which image data has not yet been collected in the current scan session, processing logic may show an outline of these regions based on data from the historical template.

At block 418, processing logic determines whether the current scan session is complete. If the scan session is not complete, the method returns to block 404 and another new image of the dental site is received. As new images are received, these new images may be registered to the previous images and/or to the historical template. Eventually, enough images should be generated such that all images can register to one or more other images from the current scan session. If at block 420 the scan is complete, the method continues to block 420.

At block 420, processing logic may refine the image registration between the images from the scan session. The 3D model that is generated during the scan session may be a rough model. Once the scan session is complete, a more rigorous image registration process may be performed to generate a much more accurate 3D virtual model of the dental site. The more rigorous image registration process may use more processing resources and take more time to generate than the 3D model generated during the scan session.

Figure 5:
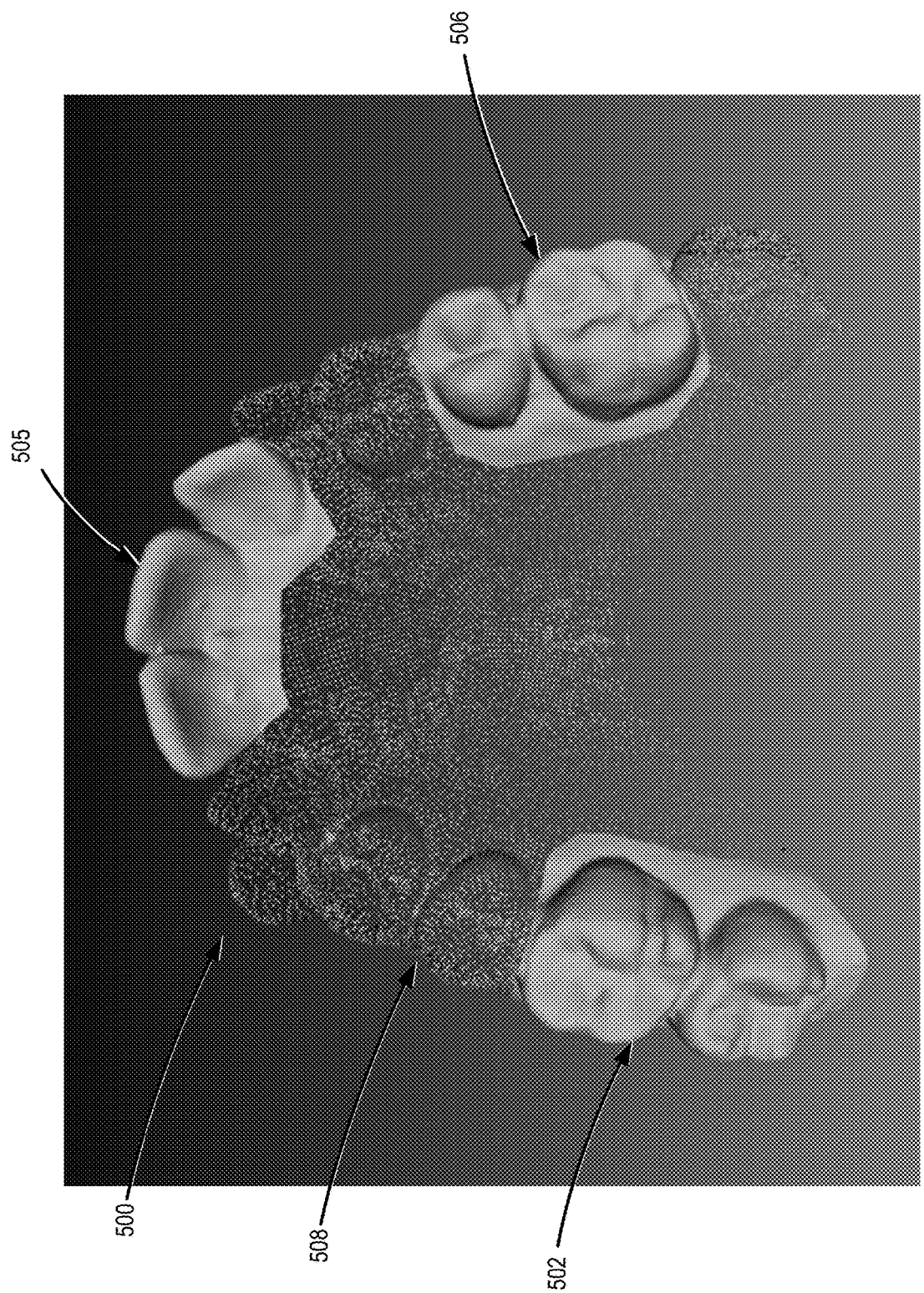
FIG. 5 illustrates a three dimensional representation of intraoral images taken during a current scan session that have been registered to a historical template, in accordance with embodiments of the present invention.

FIG. 5 illustrates a pictorial representation (e.g., a 3D virtual model 500) of a dental site that includes image data from a current scan and image data from a historical template, in accordance with embodiments of the present invention. In one embodiment, the 3D virtual model 500 includes surfaces 502-506 based on images of a current scan that are overlaid onto corresponding positions of an associated historical template 508. The surfaces 502-506 may be shown as solid surfaces.

Each of the surfaces 502-506 may be based on a single image from the current scan or based on multiple images from the current scan that have been stitched together. The images associated with surface 502 could not be appropriately registered to any of the images associated with surface 505 or surface 506 due to insufficient overlap of area between the images. Similarly, the images associated with surface 505 could not be appropriately registered to any of the images associated with surface 506 due to insufficient overlap of area between the images. However, the images associated with surfaces 502-506 may still be registered to the historical template 508. This may enable all of the images from the current scan session to be used rather than discarded. Additionally, by registering the images to the historical template, the 3D virtual model 500 may be generated that shows regions of a patient's dental site for which additional images should be generated.

In one embodiment, the regions of the dental site for which current scan data is not yet available are shown based on data from the historical template. A surface of such regions may be represented by a 3D point cloud, or may be represented as an outline or translucent surface rather than a solid surface. In one embodiment, the virtual 3D model that includes data from the historical template 508 is provided to a user with surfaces 502-506 overlaid on the historical template 508. Surfaces 502-506 may be displayed in color or filled-in (in non-3D point cloud form) so as to differentiate surfaces 502-506 based on the actual scanned images from the surfaces based on underlying historical template 508. Surfaces 502-506 based on intraoral images may be displayed on the historical template 508 in real-time, as they are being recorded. In another embodiment, data from historical template 508 is not provided for display, but surfaces 502-506 based on intraoral images are provided for display in their proper place, based on registration to the historical template 508. Surfaces 502-506 may be displayed in their proper places in real-time, without providing the 3D point cloud historical template 508 for display.

In one embodiment, restorative models may be based on historical template 508. For example, if a dental practitioner is designing a new crown for an affected area of a patient's intraoral cavity, historical templates, such as template 508, may be provided to the practitioner from a time in which the affected area was healthy. An area of the historical template may be selected as a restorative model for the crown. The model may be further adjusted, as necessary, to compete the design of the crown.

In other embodiments, when a user finalizes a scan without scanning an area that was previously scanned and present in a historical template 508, the missing area may be filled in by the corresponding data from the historical template 508. This may be represented by an area changing from display of the historical template's 3D point cloud to display of the same area being filled in (e.g., similar to surfaces 502-506). In one embodiment, the missing area may be filled in based on trends associated with more than one historical template. For example, if three historical templates exist, and each template shows a 1 mm shift in the teeth associated with an area missing from the current scan between scans, the area may be provided with an additional 1 mm shift in the teeth associated with the area.

Figure 6:
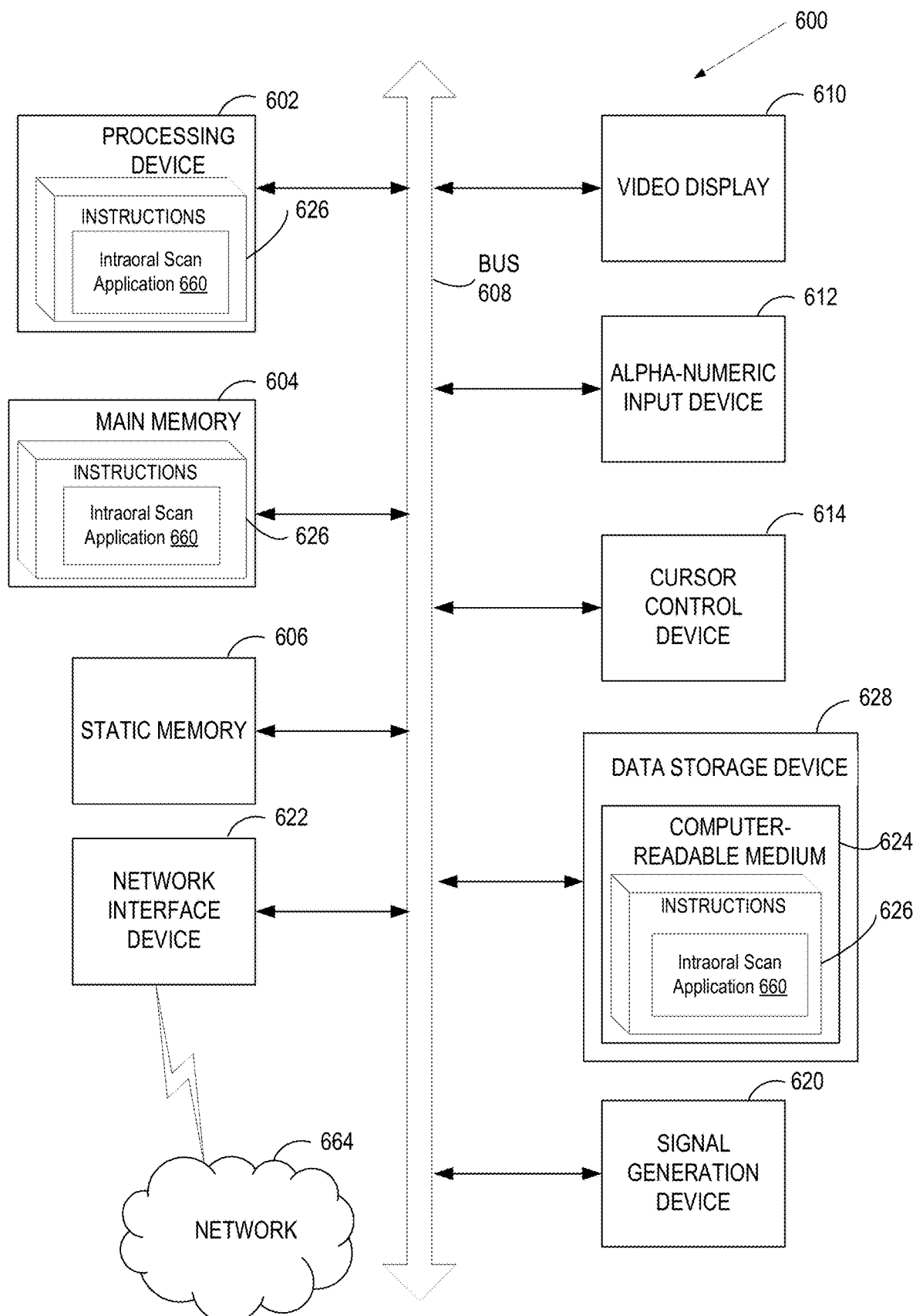
FIG. 6 illustrates a block diagram of an example computing device, in accordance with embodiments of the present invention.

FIG. 6 illustrates a diagrammatic representation of a machine in the example form of a computing device 600 within which a set of instructions, for causing the machine to perform any one or more of the methodologies discussed herein, may be executed. In alternative embodiments, the machine may be connected (e.g., networked) to other machines in a Local Area Network (LAN), an intranet, an extranet, or the Internet. The machine may operate in the capacity of a server or a client machine in a client-server network environment, or as a peer machine in a peer-to-peer (or distributed) network environment. The machine may be a personal computer (PC), a tablet computer, a set-top box (STB), a Personal Digital Assistant (PDA), a cellular telephone, a web appliance, a server, a network router, switch or bridge, or any machine capable of executing a set of instructions (sequential or otherwise) that specify actions to be taken by that machine. Further, while only a single machine is illustrated, the term "machine" shall also be taken to include any collection of machines (e.g., computers) that individually or jointly execute a set (or multiple sets) of instructions to perform any one or more of the methodologies discussed herein.

The example computing device 600 includes a processing device 602, a main memory 604 (e.g., read-only memory (ROM), flash memory, dynamic random access memory (DRAM) such as synchronous DRAM (SDRAM), etc.), a static memory 606 (e.g., flash memory, static random access memory (SRAM), etc.), and a secondary memory (e.g., a data storage device 628), which communicate with each other via a bus 608.

Processing device 602 represents one or more general-purpose processors such as a microprocessor, central processing unit, or the like. More particularly, the processing device 602 may be a complex instruction set computing (CISC) microprocessor, reduced instruction set computing (RISC) microprocessor, very long instruction word (VLIW) microprocessor, processor implementing other instruction sets, or processors implementing a combination of instruction sets. Processing device 602 may also be one or more special-purpose processing devices such as an application specific integrated circuit (ASIC), a field programmable gate array (FPGA), a digital signal processor (DSP), network processor, or the like. Processing device 602 is configured to execute the processing logic (instructions 626) for performing operations and steps discussed herein.

The computing device 600 may further include a network interface device 622 for communicating with a network 664. The computing device 600 also may include a video display unit 610 (e.g., a liquid crystal display (LCD) or a cathode ray tube (CRT)), an alphanumeric input device 612 (e.g., a keyboard), a cursor control device 614 (e.g., a mouse), and a signal generation device 620 (e.g., a speaker).

The data storage device 628 may include a machine-readable storage medium (or more specifically a non-transitory computer-readable storage medium) 624 on which is stored one or more sets of instructions 626 embodying any one or more of the methodologies or functions described herein. A non-transitory storage medium refers to a storage medium other than a carrier wave. The instructions 626 may also reside, completely or at least partially, within the main memory 604 and/or within the processing device 602 during execution thereof by the computer device 600, the main memory 604 and the processing device 602 also constituting computer-readable storage media.

The computer-readable storage medium 624 may also be used to store an intraoral scan application 650, which may correspond to the similarly named component of FIG. 1. The computer readable storage medium 624 may also store a software library containing methods for an intraoral scan application 650. While the computer-readable storage medium 624 is shown in an example embodiment to be a single medium, the term "computer-readable storage medium" should be taken to include a single medium or multiple media (e.g., a centralized or distributed database, and/or associated caches and servers) that store the one or more sets of instructions. The term "computer-readable storage medium" shall also be taken to include any medium other than a carrier wave that is capable of storing or encoding a set of instructions for execution by the machine and that cause the machine to perform any one or more of the methodologies of the present invention. The term "computer-readable storage medium" shall accordingly be taken to include, but not be limited to, solid-state memories, and optical and magnetic media.

It is to be understood that the above description is intended to be illustrative, and not restrictive. Many other embodiments will be apparent upon reading and understanding the above description. Although embodiments of the present invention have been described with reference to specific example embodiments, it will be recognized that the invention is not limited to the embodiments described, but can be practiced with modification and alteration within the spirit and scope of the appended claims. Accordingly, the specification and drawings are to be regarded in an illustrative sense rather than a restrictive sense. The scope of the invention should, therefore, be determined with reference to the appended claims, along with the full scope of equivalents to which such claims are entitled.

What is claimed is:

1. A non-transitory computer readable medium comprising instructions that, when executed by a processing device, cause the processing device to perform operations comprising:
   receiving, by the processing device, a first intraoral image of a dental site and a second intraoral image of the dental site during an intraoral scan session;
   determining, by the processing device, that the first intraoral image is associated with a first region of the dental site that does not overlap with a second region of the dental site associated with the second intraoral image;
   generating a first virtual model of the first region based on the first intraoral image;
   generating a second virtual model of the second region based on the second intraoral image;
   determining relative positions and orientations of the first virtual model and the second virtual model; and
   displaying the first virtual model and the second virtual model having the relative positions and orientations.

2. The non-transitory computer readable medium of claim 1, the operations further comprising:
   registering, by the processing device, the first intraoral image to the second intraoral image in a three-dimensional space according to a historical template.

3. The non-transitory computer readable medium of claim 2, wherein the historical template is not displayed.

4. The non-transitory computer readable medium of claim 2, wherein the historical template is a virtual model of the dental site as generated from additional intraoral images taken during a previous intraoral scan session.

5. The non-transitory computer readable medium of claim 1, the operations further comprising:
   registering the first intraoral image to a historical template at the first region of the dental site; and
   registering the second intraoral image to the historical template at the second region of the dental site;
   wherein the relative positions and orientations of the first virtual model and the second virtual model are determined based on the registering of the first intraoral image to the historical template and on the registering of the second intraoral image to the historical template.

6. The non-transitory computer readable medium of claim 5, wherein the first intraoral image and the second intraoral image are registered to the historical template using first registration criteria, the operations further comprising:
   receiving a third intraoral image during the intraoral scan session; and
   registering the third intraoral image to at least one of the first virtual model or the second virtual model using second registration criteria, wherein the second registration criteria are more restrictive than the first registration criteria.

7. The non-transitory computer readable medium of claim 1, the operations further comprising:
   determining a surface of the dental site at a third region based on a historical template, wherein the third region is between the first region and the second region and overlaps with the first region and the second region; and
   displaying the surface.

8. The non-transitory computer readable medium of claim 1, the operations further comprising:
   determining an intraoral area of interest based at least in part on the first virtual model and a historical template, wherein the intraoral area of interest comprises an area of the dental site that a) is represented in the historical template but is not represented in the first virtual model or b) is represented in the first virtual model but is not represented in the historical template; and
   displaying an indication of the intraoral area of interest.

9. The non-transitory computer readable medium of claim 1, the operations further comprising:
   comparing the first virtual model to a historical template;
   determining a difference between a previous depiction of the first region of the dental site as represented in the historical template and a current depiction of the first region of the dental site as represented in the first virtual model; and
   displaying a graphical representation of the difference between the previous depiction of the first region of the dental site and the current depiction of the first region of the dental site.

10. A non-transitory computer readable medium comprising instructions that, when executed by a processing device, cause the processing device to perform operations comprising:
    receiving, by the processing device, first intraoral scan data of a first segment of a dental site;
    generating a first virtual model of the first segment using the first intraoral scan data;
    receiving, by the processing device, second intraoral scan data of a second segment of the dental site that does not stitch to the first intraoral scan data or the first virtual model of the first segment of the dental site;
    generating a second virtual model of the second segment using the second intraoral scan data;

determining a spatial relationship of the first virtual model and the second virtual model; and displaying the first virtual model and the second virtual model in the spatial relationship.

11. The non-transitory computer readable medium of claim 10, the operations further comprising:

generating a combined virtual model comprising a combination of the first virtual model and the second virtual model, wherein the first virtual model and the second virtual model have the spatial relationship in the combined virtual model.

12. The non-transitory computer readable medium of claim 11, wherein generating the combined virtual model includes registering data associated with the first virtual model and data associated with the second virtual model to a historical template, wherein displaying the first virtual model and the second virtual model comprises displaying the combined virtual model, wherein the historical template is not displayed.

13. The non-transitory computer readable medium of claim 10, the operations further comprising:

determining, by the processing device, that the first segment represented in the first intraoral scan data does not overlap the second segment represented in the second intraoral scan data.

14. The non-transitory computer readable medium of claim 10, the operations further comprising:

attempting to stitch the first intraoral scan data to the second intraoral scan data; and determining that the first intraoral scan data fails to stitch to the second intraoral scan data.

15. The non-transitory computer readable medium of claim 10, the operations further comprising:

determining relative positions and orientations of the first virtual model and the second virtual model.

16. The non-transitory computer readable medium of claim 10, wherein the first intraoral scan data comprises a first plurality of intraoral images and the second intraoral scan data comprises a second plurality of intraoral images, the operations further comprising:

generating the first virtual model based on stitching the first plurality of intraoral images together; and generating the second virtual model based on stitching the second plurality of intraoral images together.

17. The non-transitory computer readable medium of claim 16, wherein arranging the spatial relationship of the first virtual model and the second virtual model comprises:

registering the first intraoral scan data with a historical template to determine a position and orientation of the first virtual model in a common reference frame; and registering the second intraoral scan data with the historical template to determine a position and orientation of the second virtual model in the common reference frame.

18. A system comprising:

an intraoral scanner to generate a plurality of intraoral images of a dental site; and a computing device comprising a memory and a processor, the computing device operatively connected to the intraoral scanner, wherein the computing device is to:

receive the plurality of intraoral images of the dental site during an intraoral scan session;

determine that a first region of the dental site represented in a first intraoral image of the plurality of intraoral images does not overlap with a second region of the dental site represented in one or more remaining intraoral images of the plurality of intraoral images;

generate a first surface of the first region of the dental site based on the first intraoral image;

generate a second surface of the second region of the dental site based on the one or more of the remaining intraoral images;

determine relative positions and orientations of the first surface and the second surface; and output the first surface and the second surface having the relative positions and orientations to a display.

19. The system of claim 18, wherein the computing device is further to:

register the first intraoral image to the one or more of the remaining intraoral images in a three-dimensional space according to a historical template, wherein the historical template is a virtual model of the dental site as generated from additional intraoral images taken during a previous intraoral scan session.

20. The system of claim 19, wherein the computing device is further to:

register the first intraoral image to the historical template at the first region of the dental site; and register the one or more remaining intraoral images to the historical template at the second region of the dental site.

* * * * *

UNITED STATES PATENT AND TRADEMARK OFFICE
CERTIFICATE OF CORRECTION

PATENT NO. : 11,276,168 B2  
APPLICATION NO. : 16/808239  
DATED : March 15, 2022  
INVENTOR(S) : Sabina et al.

Page 1 of 1

It is certified that error appears in the above-identified patent and that said Letters Patent is hereby corrected as shown below:

On the Title Page

Item (63), delete "Oct 9, 2019" and insert -- Oct 9, 2018 --

Signed and Sealed this  
Twelfth Day of April, 2022

Drew Hirshfeld  
*Performing the Functions and Duties of the*  
*Under Secretary of Commerce for Intellectual Property and*  
*Director of the United States Patent and Trademark Office*